(12) United States Patent
Sperl et al.

(10) Patent No.: US 9,330,456 B2
(45) Date of Patent: May 3, 2016

(54) SYSTEMS AND METHODS FOR REGULARIZED FOURIER ANALYSIS IN X-RAY PHASE CONTRAST IMAGING

(71) Applicant: General Electric Company, Schenectady, NY (US)

(72) Inventors: Jonathan Immanuel Sperl, Garching b. Munchen (DE); Kinan Mahdi, Garching b. Munchen (DE)

(73) Assignee: General Electric Company, Niskayuna, NY (US)

( * ) Notice: Subject to any disclaimer, the term of this patent is extended or adjusted under 35 U.S.C. 154(b) by 7 days.

(21) Appl. No.: 14/264,689

(22) Filed: Apr. 29, 2014

(65) Prior Publication Data

US 2015/0310609 A1    Oct. 29, 2015

(51) Int. Cl.
| | |
|---|---|
| G06K 9/00 | (2006.01) |
| G06T 7/00 | (2006.01) |
| A61B 6/00 | (2006.01) |
| G01N 23/04 | (2006.01) |
| G06K 9/52 | (2006.01) |

(52) U.S. Cl.
CPC .............. *G06T 7/0012* (2013.01); *A61B 6/484* (2013.01); *A61B 6/5205* (2013.01); *A61B 6/5211* (2013.01); *G01N 23/04* (2013.01); *G06K 9/52* (2013.01); *G06T 2207/10116* (2013.01)

(58) Field of Classification Search
CPC .................. G06T 5/001; G06T 11/003; G06T 2207/10116; G06T 5/10; G06T 7/0012; A61B 6/484; G01N 2223/419; G01N 2223/612; G01N 23/046
See application file for complete search history.

(56) References Cited

U.S. PATENT DOCUMENTS

| | | | |
|---|---|---|---|
| 6,754,298 B2 | 6/2004 | Fessler | |
| 8,229,199 B2 | 7/2012 | Chen et al. | |
| 8,246,543 B2 | 8/2012 | Johnson et al. | |
| 8,340,388 B2 | 12/2012 | Rosenstengel | |
| 8,989,347 B2 * | 3/2015 | Sperl et al. | 378/62 |
| 9,014,333 B2 * | 4/2015 | Sperl et al. | 378/62 |
| 2010/0128958 A1 | 5/2010 | Chen et al. | |
| 2010/0284596 A1 | 11/2010 | Miao et al. | |

FOREIGN PATENT DOCUMENTS

CN    102867294 A    1/2013

OTHER PUBLICATIONS

Lyuboshenko et al., "Stable signal and image reconstruction from noisy Fourier transform phase", Signal Processing, IEEE Transactions on Signal Processing, vol. 47, No. 1, Jan. 1999, (pp. 244-250, 7 pages total).

(Continued)

*Primary Examiner* — Tom Y Lu
(74) *Attorney, Agent, or Firm* — Robert M. McCarthy (57) ABSTRACT

A method of regularization of x-ray phase contrast imaging (XPCi) system measurement data includes obtaining air scan data of the XPCi system prior to the presence of an object undergoing imaging, performing Fourier analysis of the air scan data, computing air coefficients from the result of the performing step, obtaining object scan data of an object undergoing imaging on the XPCi system, regularizing the object scan data, and calculating at least one of absorption image data, differential phase image data, and dark field image data by using object coefficients. A system configured to implement the method and a non-transitory computer-readable medium are disclosed.

15 Claims, 6 Drawing Sheets

(56) References Cited

OTHER PUBLICATIONS

Stanley et al., "An Iterative Regularization Method for Total Variation-Based Image Restoration", Multiscale Model. Simul, vol. 4, No. 2, 2005, (pp. 460-489, 30 pages total).

Zhou et al., "Application of Fourier-wavelet regularized deconvolution for improving image quality of free space propagation x-ray phase contrast imaging.", Phys Med Biol., vol. 57, Issue 22, 2012, (pp. 7459-7579, 21 pages total).

* cited by examiner

SYSTEMS AND METHODS FOR REGULARIZED FOURIER ANALYSIS IN X-RAY PHASE CONTRAST IMAGING

BACKGROUND

X-ray phase contrast imaging (XPCi) creates images of an object utilizing changes in the phase of an x-ray beam as it passes through the object. XPCi improves over problems with conventional x-ray imaging, where poor image contrast can arise from small attenuation differences. Its application can be found in medicine (e.g., breast tissue tumors) and industrial applications. Because many substances induce a phase shift in the x-rays as they pass through an object, the detection of features not discernable by conventional x-ray imaging is possible with XPCi. The phase shift can be measured using an interferometer to obtain high-contrast data for low-absorption objects.

Figure 1:
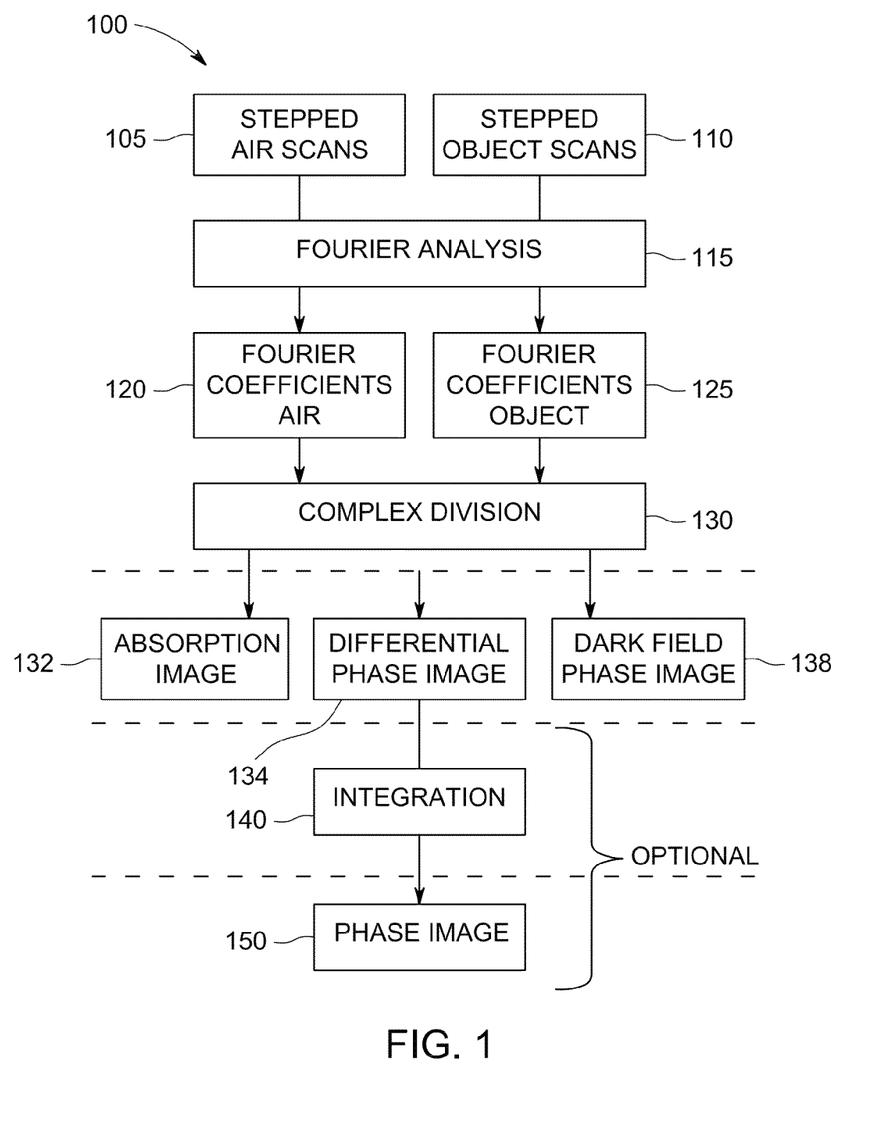
FIG. 1 depicts a standard XPCi imaging process.

FIG. 1 depicts standard XPCi imaging process 100. One implementation of XPCi is a grating based technique, where a series of images is acquired along with a grating stepping technique in order to sample the interference patterns (i.e., fringes) for each detector pixel (x,y). To correct for system non-homogeneities, sampling is performed for an air scan 105 to create a reference of system contributions. An object scan 110 is performed to collect data for imaging.

The fringes can be well approximated as a sinusoidal curve. This curve is analyzed by performing Fourier analysis 115. The Fourier analysis computes for the air scan and the object scan the first two (complex) Fourier coefficients a(x,y,0) and a(x,y,1) (0th and 1st order, respectively) 120, 125. In principle the analysis is not limited to the first two coefficients but can be done up to order N. An exemplary, conventional formulation for process 100 can be expressed as $$\min_\rho \| \mathcal{F}^H \rho - b(x,y,\cdot) \|^2 \Rightarrow a(x,y,\cdot) = \rho \quad (\text{EQ.1})$$

where (x, y) is pixel position;
$\mathcal{F}$ the Fourier transform up to order N; and
$\mathcal{F}^H$ is the adjoint of $\mathcal{F}$.

Since $\mathcal{F}$ is an orthogonal operator, the adjoint equals the inverse Fourier transform, and equation 1 can be solved directly as $a(x,y,\cdot) = \mathcal{F} b(x,y,\cdot)$ The three types of contrast provided by XPCi (i.e., absorption image att(x,y) 132, differential phase image dpc(x,y) 134, and dark field image dci(x,y) 138), can be computed by a complex division 130 of the Fourier coefficients of the object scan by the Fourier coefficients of the air scan, as follows $$p(x, y, n) = \frac{a_{obj}(x, y, n)}{a_{air}(x, y, n)}, n = 0 \ldots N \quad (\text{EQ. 2})$$

$$att(x, y) = |p(x, y, 0)| \quad (\text{EQ. 3})$$

$$dpc(x, y) = \sphericalangle (p(x, y, 1)) \quad (\text{EQ. 4})$$

$$dci(x, y) = \frac{\sum_{n=1,3,5,\ldots,N} |p(x, y, n)|}{|p(x, y, 0)|} \quad (\text{EQ. 5})$$

Subsequently, phase image 150 can be computed by integrating 140 the differential phase image 123 on a line-by-line basis. However, integration step 140 is an optional part of the process.

Advanced processing strategies of XPCi images (e.g., regularization/de-noising using neighboring pixels/rows, etc.) have only been applied to the later steps of conventional process 100.

DETAILED DESCRIPTION

In accordance with embodiments, regularization of XPCi imaging is applied to the beginning and central steps of the XPCi imaging process. In particular, the Fourier analysis step uses the air scan Fourier coefficients as correction factors for the analysis of the object scan. Rather than independently computing Fourier coefficients for each detector pixel, prior knowledge about the object undergoing imaging is incorporated into embodying methods to yield a global image reconstruction. For example, knowing that neighboring pixels are not completely independent from one another is sufficient prior knowledge about the object. In accordance with implementations, the choices for the regularizers can include total variation, wavelet sparsity, dictionary sparsity, etc.—each of which can act on the complex coefficients, their magnitude, and/or their phase terms.

In accordance with embodiments, the pixel cost function is globalized by a regularization term that incorporates prior knowledge (e.g., model assumptions) about the object. The optimization problem can then be solved using any numerical solver for unconstrained optimization, in particular a dedicated iterative shrinkage/thresholding algorithm.

Figure 2:
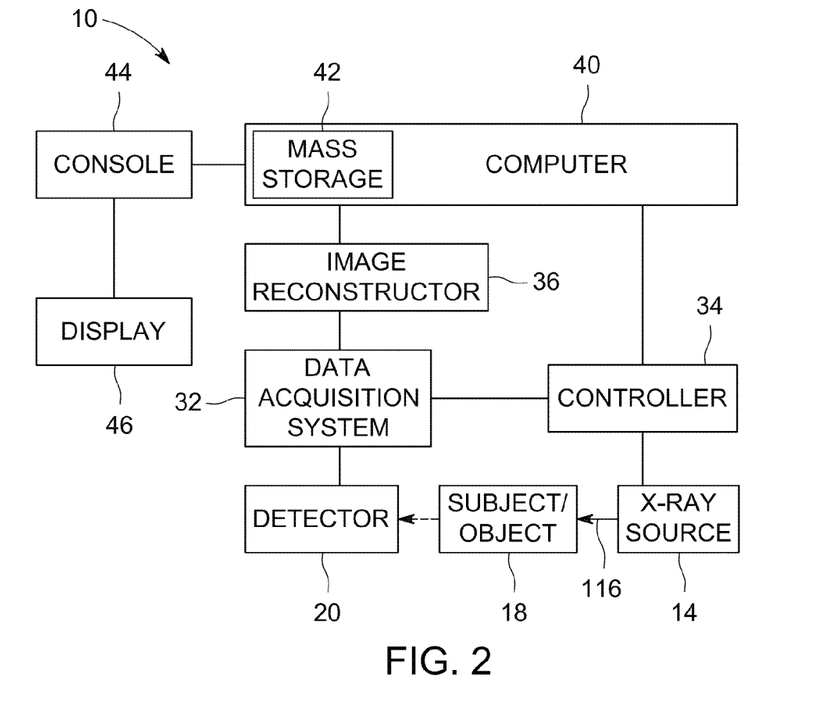
FIG. 2 depicts an X-ray imaging system in accordance with some embodiments.

FIG. 2 illustrates X-ray imaging system 10 including an X-ray source 14 that projects a beam of X-rays 16 through a subject 18 (e.g., a patient, object, sample, etc.) toward one or more detectors 20. The detector 20 is coupled to a data acquisition system 32. The one or more detectors 20 sense the transmitted X-rays that pass through the subject 18, and the data acquisition system 32 converts the sensed X rays to digital signals for subsequent processing. Each detector 20 produces an electrical signal that represents the intensity of an impinging X-ray beam after it passes through the subject 18. The operation of the X-ray source 14 may be governed by an X-ray controller 34 that provides power and timing signals to the X-ray source 14. An image reconstructor 36 receives sampled and digitized X-ray data from the data acquisition system 32 and performs reconstructions to produce phase contrast images. The reconstructed image is applied as an input to a processor based computer 40 that stores the image in a mass storage device 42.

The computer 40 also receives commands and scanning parameters from an operator via a console 44 that has some form of operator interface, such as a keyboard, mouse, voice activated controller, or any other suitable input apparatus. An associated display 46 enables the operator to observe the reconstructed images and other data from the computer 40. The operator-supplied commands and parameters are used by the computer 40 to provide control signals and information to the data acquisition system 32 and the X-ray controller 34.

Figure 3:
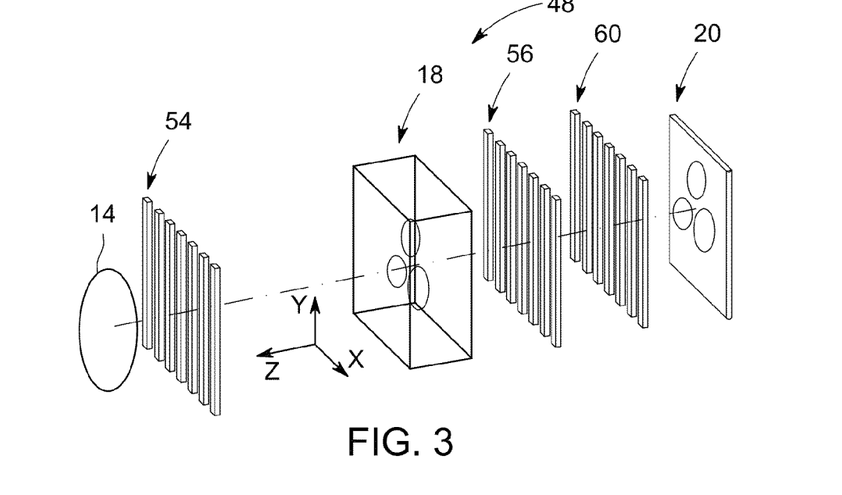
FIG. 3 depicts a differential XPC imaging setup in accordance with some embodiments.

FIG. 3 illustrates a differential XPC imaging setup 48 in which a spatially coherent X-ray beam is used to probe an object (or subject) 18. An incoherent X-ray source 14 is provided with a blocking grating 54 to create the coherent X-ray beam. In accordance with other implementations, the spatially coherent X-ray beam may be realized by synchrotron radiation, a micro focus X-ray source, or any other suitable source. A spatially coherent X-ray beam passes a phase grating 56, and periodic interference patterns or fringes are generated. The patterns' period is typically in the order of a few microns, an interferometric technique is applied to analyze the fringes using an X-ray detector 20 (e.g., having a pixel in the order of a few 100 µm). Another blocking grating 60 having the same period as the fringes is placed in front of the detector 20.

During operation of the illustrated imaging setup 48, in a series of steps, grating 56 or grating 60 are shifted by a fraction of its period in the direction orthogonal to the grating slits, and images are taken for each position. After covering the entire period, the measurements for each detector pixel may be described as the convolution of the fringes with the rectangular grating function. Using Fourier analysis, the phase, the mean value and the oscillation amplitude of the fringes are determined. During an imaging operation, in addition to the gratings 56 and 60, the object or subject 18 is placed into the X-ray beam, and the X-rays are refracted by the object 18 and hence undergo an additional phase shift. By repeating the measurement procedure, the phase of the shifted fringes is detected and the difference of both measurements yields the phase shift due to the object 18. The differential XPC measurement generates projections of the gradient of the cumulative phase shift due to refractive index variability of the object in a direction orthogonal to the X-ray beam and to the grating slits.

Figure 4:
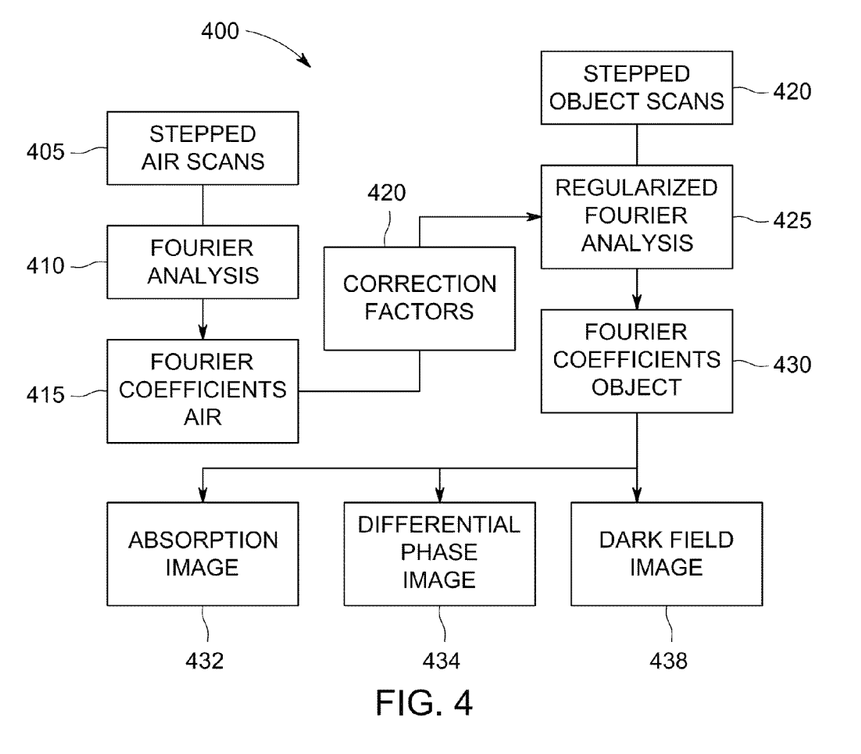
FIG. 4 depicts an XPCi imaging process in accordance with some embodiments.

FIG. 4 depicts XPCi imaging process 400 in accordance with some embodiments. Imaging process 400 applies regularized Fourier analysis to first and central steps in the imaging process. To correct for system non-homogeneities, process 400 obtains air scans, step 405, of the system prior to the presence of the object undergoing imaging. Fourier analysis of the air scans is performed, step 410. From the Fourier analysis, air coefficients can be computed, step 415. After the object undergoing imaging is placed in the system, object scans can be obtained, step 420.

Fourier analysis of the object scans is regularized, step 425. Regularization uses the prior knowledge of the object (i.e., assumptions that the object measured is not completely random). By assuming 'non-randomness' of the object, potential regularizations can include total variation (e.g., the object has some smoothness properties) and wavelet domain sparsity (e.g., the object contains somewhat coherent structures due to the non-randomness). In accordance with other implementations, other regularizations can be used. In accordance with embodiments, once the regularized reconstruction is formulated, the solution is a global optimization problem—i.e., no longer a pixel-by-pixel approach.

Regularization is done by incorporating prior object knowledge, e.g., by adding terms to the cost function. The correction factors are used to employ the regularization in a proper way. Object prior knowledge can be exploited for the real physical object, and not for the physical object confounded by inhomogeneity factors due to the system.

Fourier analysis of the regularized object scans is performed, step 430, to obtain object coefficients. In accordance with embodiments, the regularized Fourier analysis directly results, step 430, in the coefficients p(x,y,n) (as opposed to the conventional coefficients $a_{obj}(x,y,n)$), from which absorption image 432, differential phase image 434, and dark field image 438 can be calculated—see Equations 3-5 (above).

Equation 6 (below) includes a regularization function, but does not take system non-homogeneities into account, and is confounded by variation across the detector (i.e., regularization is not optimal).

$$\min_a \Sigma_{x,y} \| \mathcal{F}^H a(x,y,\bullet) - b(x,y,\bullet) \|^2 + \Sigma_{n=0}^N \mathcal{R}_n(a(\bullet,\bullet,n)) \quad (EQ.6)$$

where, b(x,y,s) is measured data for x, y detector row/column;

s is grating step;

$\mathcal{F}$ is Fourier basis up to order N (typically N=1);

a(x,y,n) is the Fourier coefficients for object scan (order n); and $\mathcal{R}_n$ is the regularizer function (e.g., total variation, wavelet sparsity, dictionary sparsity, etc. —which act on the complex coefficients, their magnitude and/or their phase terms).

In accordance with an embodiment, correction factors from the air reference scan are inserted into data obtained from the object scan. By inserting the reference scan correction factors there are less steps needed to obtain accurate imaging data, thus less exposure (i.e., dosage) to the x-rays for the same scan obtained by conventional XPCi techniques. Alternately, for the same exposure an improved image (i.e., higher image quality) can be obtained. This approach can be expressed as Equation 7:

$$\min_a \Sigma_{x,y} \| \mathcal{F}^H (Cp)(x,y,\bullet) - b(x,y,\bullet) \|^2 + \Sigma_{n=0}^N \mathcal{R}_n (p(\bullet,\bullet,n)) \quad (EQ.7)$$

where $(Cp)(x,y,n) = a_{air}(x,y,n) p(x,y,n)$ is the operator to uncorrect p.

Equations 6 and 7 can be solved iteratively (e.g., using an iterative shrinkage/thresholding algorithm (ISTA) or other iterative approach).

Figure 5A:
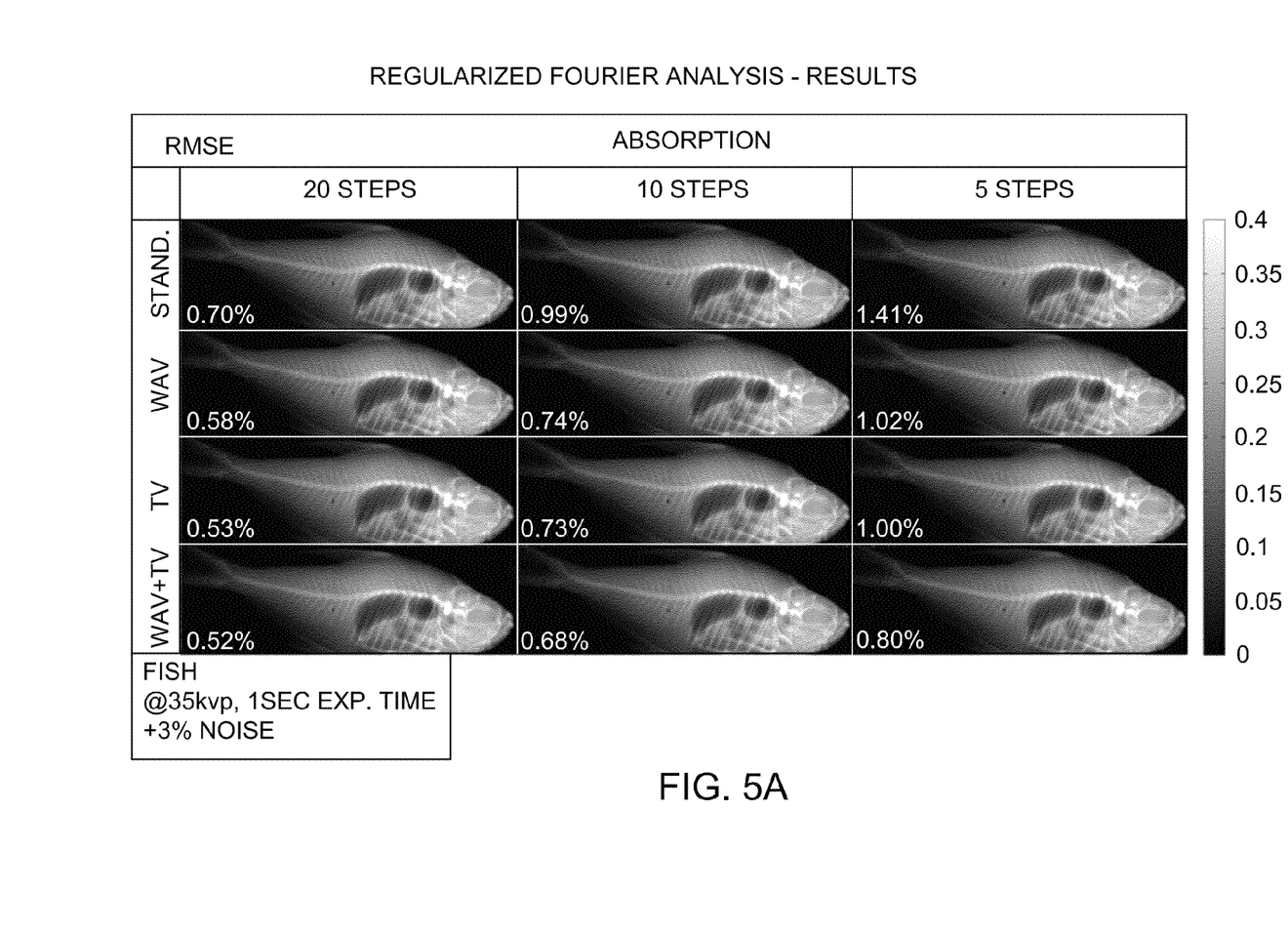
FIGS. 5A-5C depict regularized Fourier analysis image contrast results for an object obtained using an XPCi system in accordance with some embodiments.
Figure 5B:
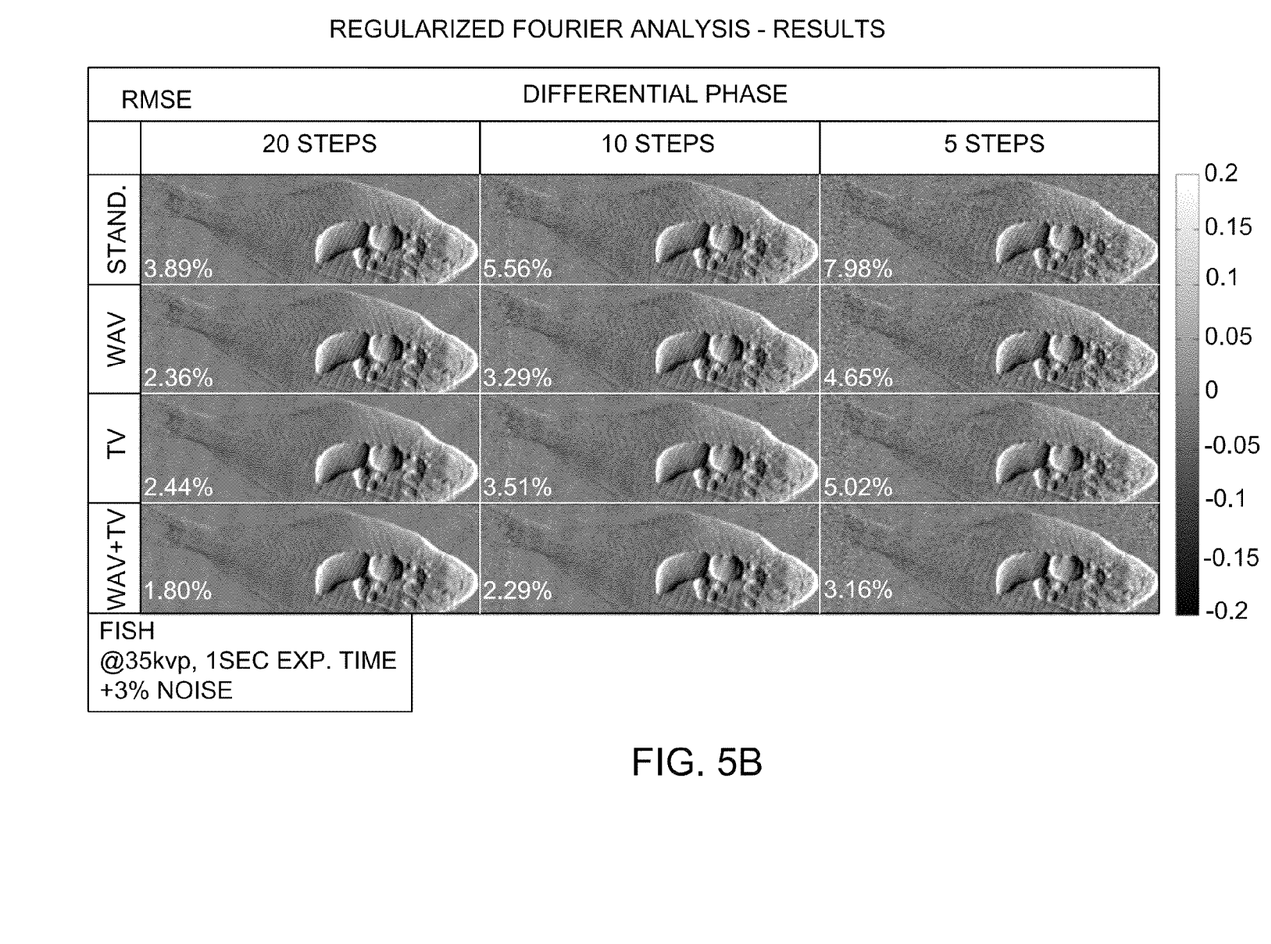
Figure 5C:
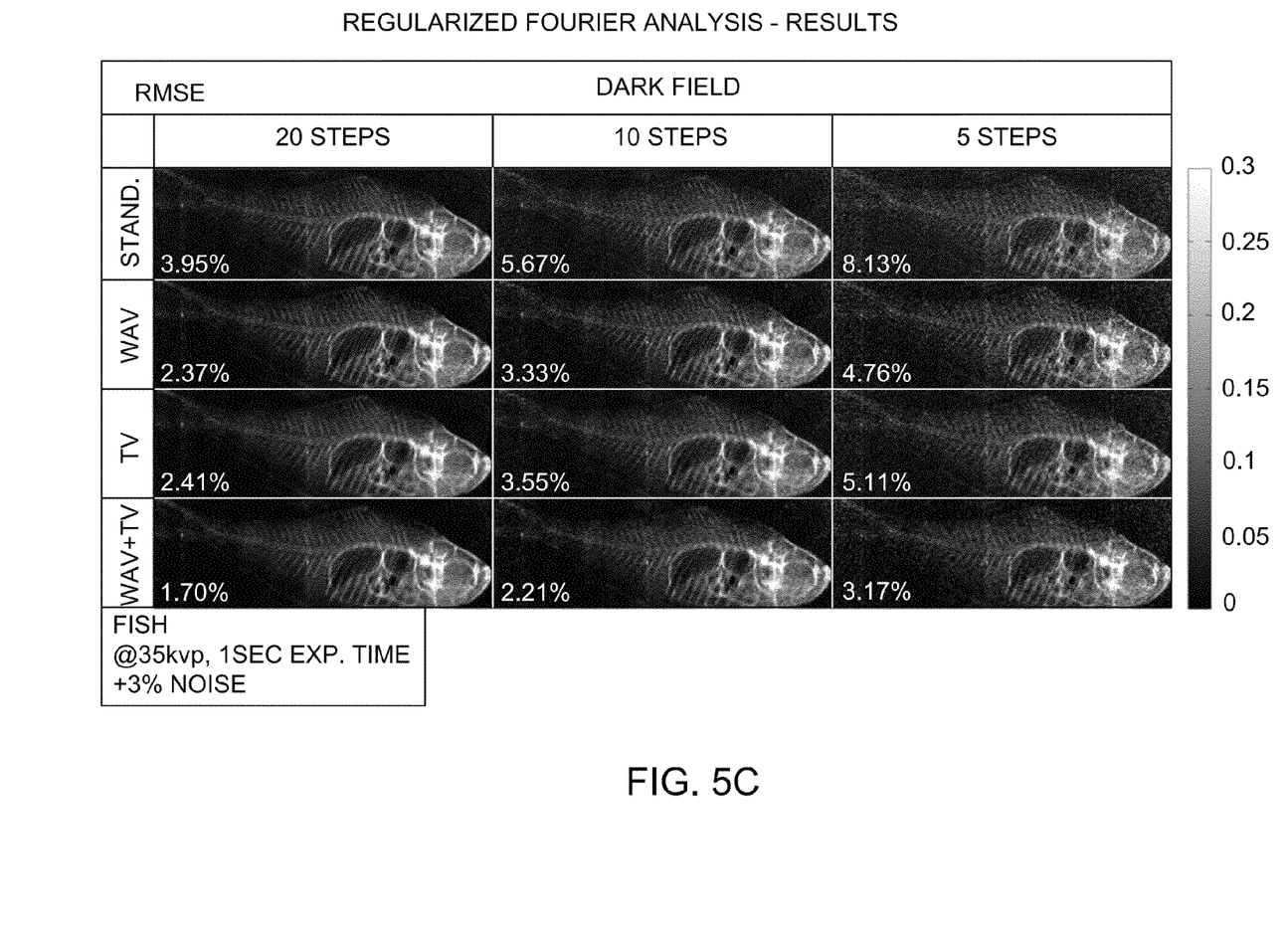

FIGS. 5A-5C depict regularized Fourier analysis image contrast results for an object obtained using an XPCi system in accordance with some embodiments. Measurements were taken with 20 steps (i.e., scans) (left column); 10 steps (middle column): and 5 steps (right column). The object, a fish, was measured under the same conditions (i.e., @35 kVp, 1 sec exp. Time, +3% noise (which was added artificially to highlight the de-noising properties of the embodying method)) using standard XPCi processing (first row); embodying XPCi processing with wavelet regularization (second row); embodying XPCi processing with total variation regularization (third row); and embodying XPCi processing with wavelet plus total variation regularization (fourth row). FIG. 5A depicts the absorption image contrast results. FIG. 5B depicts the differential phase image contrast results. FIG. 5C depicts the dark field image contrast results. The percentages within each image represent the root-mean-square error (RMSE) from a high-quality scan (40 steps with no noise added). As can be seen from FIGS. 5A-5C, embodying XPCi processing in accordance with embodiments produces contrast images that have lower RMSE values than the standard approach for the same number of steps. Further, in some instances embodying XPCi processing can produce lower RMSE values in fewer steps when compared to the standard XPCi processing. Accordingly, embodying XPCi processing can lower the dosage exposure of patients and still yield acceptable, or even improved, results.

In accordance with some embodiments, a computer program application stored in non-volatile memory or computer-readable medium (e.g., register memory, processor cache, RAM, ROM, hard drive, flash memory, CD ROM, magnetic media, etc.) may include code or executable instructions that when executed may instruct and/or cause a controller or processor to perform methods discussed herein such as a method for regularization of XPCi imaging by exploiting prior knowledge of the object to the beginning and central steps of the XPCi imaging process, as described above.

The computer-readable medium may be a non-transitory computer-readable media including all forms and types of memory and all computer-readable media except for a transitory, propagating signal. In one implementation, the non-volatile memory or computer-readable medium may be external memory.

Although specific hardware and methods have been described herein, note that any number of other configurations may be provided in accordance with embodiments of the invention. Thus, while there have been shown, described, and pointed out fundamental novel features of the invention, it will be understood that various omissions, substitutions, and changes in the form and details of the illustrated embodiments, and in their operation, may be made by those skilled in the art without departing from the spirit and scope of the invention. Substitutions of elements from one embodiment to another are also fully intended and contemplated. The invention is defined solely with regard to the claims appended hereto, and equivalents of the recitations therein.

The invention claimed is:

1. A method of regularization of x-ray phase contrast imaging (XPCi) system measurement data, the method comprising:
   performing a scan utilizing the XPCi system prior to the presence of an object undergoing imaging to generate air scan data;
   obtaining the air scan data of the XPCi system;
   performing Fourier analysis of the air scan data;
   computing air coefficients from the result of the performing step;
   scanning an object utilizing the XPCi system to generate object scan data;
   obtaining object scan data of an object undergoing imaging on the XPCi system;
   regularizing the object scan data; and
   calculating at least one of absorption image data, differential phase image data, and dark field image data by using object coefficients.

2. The method of claim 1, wherein the air coefficients represent system non-homogeneity factors.

3. The method of claim 1, including applying Fourier analysis to the object scan data to perform the regularizing step.

4. The method of claim 1, the regularizing step including using prior knowledge of the object undergoing imaging.

5. The method of claim 1, wherein the regularizing step includes applying a regularizer function, the regularizer function being one of total variation, wavelet sparsity, and dictionary sparsity.

6. A non-transitory computer-readable medium having stored thereon instructions which when executed by a processor cause the processor to perform a method of regularization of x-ray phase contrast imaging (XPCi) system measurement data, the method comprising:
   obtaining air scan data of the XPCi system prior to the presence of an object undergoing imaging;
   performing Fourier analysis of the air scan data;
   computing air coefficients from the result of the performing step;
   obtaining object scan data of an object undergoing imaging on the XPCi system;
   regularizing the object scan data; and
   calculating at least one of absorption image data, differential phase image data, and dark field image data by using object coefficients.

7. The medium of claim 6, wherein the air coefficients represent system non-homogeneity factors.

8. The medium of claim 6, including instructions to cause the processor to perform the step of applying Fourier analysis to the object scan data to perform the regularizing step.

9. The medium of claim 6, including instructions to cause the processor to perform the regularizing step by including using prior knowledge of the object undergoing imaging.

10. The medium of claim 6, wherein the regularizing step includes applying a regularizer function, the regularizer function being one of total variation, wavelet sparsity, and dictionary sparsity.

11. A system for regularization of x-ray phase contrast imaging (XPCi) system measurement data, the system comprising:
    an X-ray source configured to generate an X-ray beam directed toward the subject;
    a detector that in operation configured to detect at least a portion of the X-ray beam and to produce a signal corresponding to the detected portion of the X-ray beam;
    a grating system comprising one or more gratings located between the X-ray source and the detector;
    a control processor configured to receive the signal from the detector and to execute computer-readable instructions that cause the control processor to perform a method including:
    obtaining air scan data of the XPCi system prior to the presence of an object undergoing imaging;
    performing Fourier analysis of the air scan data;
    computing air coefficients from the result of the performing step;
    obtaining object scan data of an object undergoing imaging on the XPCi system;
    regularizing the object scan data; and
    calculating at least one of absorption image data, differential phase image data, and dark field image data by using object coefficients.

12. The system of claim 11, wherein the air coefficients represent system non-homogeneity factors.

13. The system of claim 11, including instructions to cause the processor to perform the step of applying Fourier analysis to the object scan data to perform the regularizing step.

14. The system of claim 11, including instructions to cause the processor to perform the regularizing step by including using prior knowledge of the object undergoing imaging.

15. The system of claim 11, wherein the regularizing step includes applying a regularizer function, the regularizer function being one of total variation, wavelet sparsity, and dictionary sparsity.

* * * * *